US010760418B1

(12) United States Patent
Liu et al.

(10) Patent No.: US 10,760,418 B1
(45) Date of Patent: Sep. 1, 2020

(54) METHOD AND SYSTEM FOR PRESERVING AND OBTAINING HYDROCARBON INFORMATION FROM ORGANIC-RICH ROCK SAMPLES

(71) Applicant: REVOCHEM LLC, Houston, TX (US)

(72) Inventors: Yifei Liu, Houston, TX (US); Jiang Wu, Houston, TX (US)

( * ) Notice: Subject to any disclaimer, the term of this patent is extended or adjusted under 35 U.S.C. 154(b) by 0 days.

(21) Appl. No.: 16/392,098

(22) Filed: Apr. 23, 2019

Related U.S. Application Data (60) Provisional application No. 62/837,119, filed on Apr. 22, 2019, provisional application No. 62/837,114, filed on Apr. 22, 2019, provisional application No. 62/671,510, filed on May 15, 2018, provisional application No. 62/661,109, filed on Apr. 23, 2018.

(51) Int. Cl.
| | | |
|---|---|---|
| *G01N 1/40* | (2006.01) | |
| *E21B 49/02* | (2006.01) | |
| *G01N 33/24* | (2006.01) | |
| *G01N 1/08* | (2006.01) | |

(52) U.S. Cl.
CPC ............... *E21B 49/02* (2013.01); *G01N 1/08* (2013.01); *G01N 1/4022* (2013.01); *G01N 33/241* (2013.01)

(58) Field of Classification Search
CPC ...... E21B 49/02; E21B 41/0092; E21B 47/00; G01N 1/08; G01N 1/4022; G01N 33/241; G01N 33/2823; G01N 30/88; G01N 30/8686; G01V 3/38
USPC ........................................................ 73/23.41
See application file for complete search history.

(56) References Cited

U.S. PATENT DOCUMENTS

| | | | | |
|---|---|---|---|---|
| 5,242,245 A | * | 9/1993 | Schellstede | B09C 1/06 110/346 |
| 5,390,529 A | * | 2/1995 | Ghiselli | G01N 33/241 73/23.41 |
| 6,649,129 B1 | * | 11/2003 | Neal | G01N 1/16 422/88 |
| 2013/0152710 A1 | * | 6/2013 | Laugharn, Jr. | G01N 1/08 73/864.91 |
| 2017/0250024 A1 | * | 8/2017 | Lewis | H01F 1/068 |

(Continued)

OTHER PUBLICATIONS

"Cryogenic quenching of rock using liquid nitrogen as a coolant: Investigation of surface effects," by Li et al., International Journal of Heat and Mass Transfer, pp. 446-459, 2018 (Year: 2018).*

*Primary Examiner* — Suman K Nath
(74) *Attorney, Agent, or Firm* — Wayne Edward Ramage; Baker Donelson (57) ABSTRACT

Methods and systems to preserve, prepare, extract, and/or analyze hydrocarbons in the pore spaces of or adsorbed in organic-rich rock samples, such as, but not limited to, drill cuttings and drill cores, using one or more combinations of physical energy sources, including, but not limited to, thermal, vapor pressure, and mechanical stress. The collected samples are transported and prepared in low temperature conditions, with parts of subsequent processing at very low temperatures, thereby allowing a fuller measurement of geochemical fingerprints for the extracted hydrocarbons using various analysis tools. More particularly, the treatment and process allows geochemical fingerprinting to very low carbon number ranges.

15 Claims, 10 Drawing Sheets

(56) References Cited

U.S. PATENT DOCUMENTS

2018/0313807 A1* 11/2018 Michael ............... G01N 33/241
2018/0340417 A1* 11/2018 Cooper .................. E21B 49/06

* cited by examiner

METHOD AND SYSTEM FOR PRESERVING AND OBTAINING HYDROCARBON INFORMATION FROM ORGANIC-RICH ROCK SAMPLES

This application claims priority to and benefit of U.S. Provisional Applications No. 62/837,119, filed Apr. 22, 2019, No. 62/837,114, filed Apr. 22, 2019, No. 62/671,510, filed May 15, 2018, and No. 62/661,109, filed Apr. 23, 2018, the complete disclosures, specifications, drawings and appendices of which are incorporated herein by specific reference in their entireties for all purposes.

FIELD OF INVENTION

This invention relates to a system and methods for collecting hydrocarbon information from organic-rich rock samples. More particularly, this invention relates to a system and methods to extract and analyze hydrocarbons trapped in the pore spaces or adsorbed in organic-rich rock samples such as, but not limited to, drill cuttings and drill cores, using one or more combinations of physical energy sources, including, but not limited to, thermal, vapor pressure, and mechanical stress.

BACKGROUND OF THE INVENTION

According to the U.S. Energy Information Administration (EIA), crude oil production from unconventional reservoirs, primarily the organic-rich shales, accounted for almost 50% of total U.S. crude oil production in 2017. The organic-rich shale typically has extremely low permeability (nano-darcy to micro-darcy) and large surface area from the kerogen where hydrocarbon absorbed to. Special extraction processes are required in order to collect hydrocarbon from those ultra-tight, organic-rich shale rock samples in the laboratory. Currently, the industry standard extraction method for organic-rich rock sample analysis is Soxhlet extraction where the rock sample is placed into an extraction thimble where it is then extracted using organic-solvent such as dichloromethane (DCM) carbon disulfide ($CS_2$), and pentane via the reflux cycle. The extracts are dissolved in the solvent forming a solution which is collected at the end of the extraction process. The solution is then blown down using thermal or vaporization procedure to remove the solvent, and the remaining extract is used for analysis. There are two critical disadvantages of the Soxlet extraction process: 1) the organic solvent is very strong and extracts all organic matter (both mobile and immobile hydrocarbon) from the rock; however, for most applications, only the mobile hydrocarbon part is of interest; 2) the blown-down process causes significant loss of the light-end of the hydrocarbon extracts due to vaporization, leading to reservation of only the heavy hydrocarbon (typically C13 and above) of the extracts from the shale rock samples.

Examples of prior art methods and system are described in the following references, all of which are incorporated herein by specific reference in their entireties for all purposes:

U.S. Pat. No. 6,661,000 B2, filed Dec. 11, 2002, entitled "Method for Measuring Absorbed and Interstitial Fluids."

U.S. No. 7,445,041 B2, filed Aug. 9, 2007, entitled "Method and System for Extraction of Hydrocarbons from Oil Shale."

U.S. No. 2010/0089132 A1, filed Feb. 30, 2008, entitled "Method and Apparatus for Obtaining Heavy Oil Samples from a Reservoir Sample."

U.S. No. 2011/0108466 A1, filed Nov. 8, 2010, entitled "Method of Separating Hydrocarbons from Oil Rocks using Ionic Liquids."

U.S. Pat. No. 9,638,821 B2, filed Mar. 16, 2015, entitled "Mapping and Monitoring of Hydraulic Fractures using Vector Magnetometers."

Crisp, Phillip T., et al., 1985, "Flash Thermal Desorption as an Alternative to Solvent Extraction for the Determination of C8-C35 Hydrocarbons in Oil Shales," Analytical Chemistry 1986, 58, pages 258-261.

Baltussen, E., et al., 2002, "Sorptive sample preparation—a review," Anal. Bioanal. Chem. Chemistry (2002), 373, pages 3-22.

Schaefer, R. G., 1985, "GC Analysis of Hydrocarbons in Sedimentary Rocks using a Commercial Thermodesorption Unit as Injection Device", Journal of High Resolution Chromatography & Chromatography Communication, Volume 8, Issue 5, Pages 267-269.

Abram, M. A., et al., 2017, "A New Thermal Extraction Protocol to Evaluate Liquid Rich Unconventional Oil In Place and In-situ Fluid Chemistry", Marine and Petroleum Geology, Volume 88, sPage 659-675.

Jiang, C., et al., 2016, "Hydrocarbon Evaporative Loss from Shale Core Samples as Revealed by Rock-Eval and Thermal Desorption—Gas Chromatography Analysis: Its Geochemical and Geological Implications", Marine and Petroleum Geology, Volume 70, Pages 294-303.

Piotrowski, Paulina K., et al., 2018, "Applications of thermal desorption coupled to comprehensive two-dimensional gas chromatography/time-of-flight mass spectrometry for hydrocarbon fingerprinting of hydraulically fractured shale rocks," Journal of Chromatography A, 1579, pages 99-105.

Piotrowski, Paulina K., et al., 2018, "Elucidating Environmental Fingerprinting Mechanisms of Unconventional Gas Development through Hydrocarbon Analysis," Analytical Chemistry 2018, 90, pages 5466-5473.

Piotrowski, Paulina K., et al., 2017, "Non-Targeted chemical characterization of a Marcellus shale gas well through GC×GC with scripting algorithms and high-resolution time-offlight mass spectrometry," Fuel 215 (2018), pages 363-369.

SUMMARY OF THE INVENTION

The methods and system disclosed herein provides a fundamentally different type of hydrocarbon extraction process from organic-rich rock samples that overcomes the disadvantages associated with the Soxhlet extraction using organic solvent. The samples are prepared and extracted in the laboratory using a thermal desorption process in which the programmed heating releases mobile hydrocarbon in the samples into the carrier-gas stream which sweeps through the samples at high vapor pressure. The released hydrocarbon is then analyzed using various geochemical fingerprinting instruments, including, but not limited to, gas chromatography (GC), 2D gas chromatography (2D-GC), gas chromatography mass spectrometry (GCMS), excitation-emission matrix spectroscopy (EEMS), inductively coupled plasma-optical emission spectrometry (ICP-OES), triple quadruple inductively coupled plasma-mass spectrometry (ICP-MS), and other similar instruments known in the art. Using the herein-described methods and system, light-end hydrocarbons stored in the shale rock samples can be preserved as low as carbon number 3 range, and the extracted hydrocarbon is a better representation of the mobile hydrocarbon portion in the organic-rich rock samples than results using Soxhlet extraction with organic solvent.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein.

DETAILED DESCRIPTION OF EXEMPLARY EMBODIMENTS

The present invention comprises methods and systems to preserve, prepare, extract, and/or analyze hydrocarbons in the pore spaces of or adsorbed in organic-rich rock samples, such as, but not limited to, drill cuttings and drill cores, using one or more combinations of physical energy sources, including, but not limited to, thermal, vapor pressure, and mechanical stress. When describing the present invention, all terms not defined herein have their common art-recognized meanings. To the extent that the following description is of a specific embodiment, a preferred embodiment, or a particular use of the invention, it is intended to be illustrative only, and is not to be construed as limiting the scope of the invention. The following description is intended to cover all alternatives, modifications and equivalents that are included in the spirit and scope of the invention, as defined in the appended claims.

In one exemplary embodiment, the system comprises means for obtaining hydrocarbon from an organic-rich rock sample, such as, but not limited to, a shale core sample or drill cuttings, that enable measurement of geochemical fingerprints using various analysis tools. Analysis tools include, but are not limited to, comprehensive two-dimensional gas chromatography with mass spectrometry (GC×GC-MS), comprehensive two-dimensional liquid chromatography (LC×LC), gas chromatography with isotope ratio mass spectrometry (GC-IRMS), fluorescence spectrometry, and electromagnetic scattering spectroscopic measurement such as Ramen spectroscopy. The samples obtained, preserved, and prepared in accordance with the invention are of high quality such that subsequent geochemical fingerprinting analyses on the samples can provide effective information on the organic-rick rock or shale reservoir performance to assist operators in achieving optimized reservoir development plan. Hydrocarbon information obtained from extracted hydrocarbons include, but is not limited to: organic compound absolute concentration; organic compound absolute mass; organic compound relative concentration; organic compound relative mass; derived fluid properties (e.g., API gravity, viscosity, gas-oil ration, and the like); elemental (e.g., sulfur, oxygen, boron) absolute concentration; elemental relative concentration; elemental absolute mass; elemental relative mass; and elemental isotopic ratios (such as, but not limited to, D/H, $^{13}C/^{12}Cu$, and $^{10}B/^{11}B$, and the like).

In one embodiment, hydrocarbon information collected from the organic-rich rock samples using the invention herein is used to calculate a group of subsurface reservoir characterization indices to provide reservoir rock permeability, fluid viscosity, water saturation, and oil saturation information to make optimal landing zone decision. In another embodiment, chemical compound information of the hydrocarbon extracted from selected organic-rich rock samples using the method described herein is used to establish a baseline to enable production allocation in an unconventional reservoir.

Because in some exemplary embodiments the present invention extracts hydrocarbon from a rock sample through a thermal desorption process, the terms "desorption", "desorption unit", or "desorbed hydrocarbon" may be used herein to denote the extraction process, the extraction device, or the extracted hydrocarbon, respectively.

Figure 1:
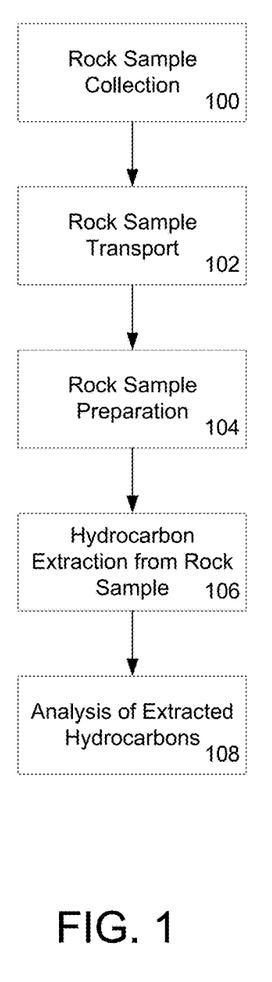
FIG. 1 is a flowchart illustrating the basic steps of several exemplary embodiments of the present inventive methods, directed towards collecting hydrocarbon information from organic-rich rock sample.

FIG. 1 is a flowchart illustrating the basic steps of some exemplary embodiments of the present invention, directed towards collecting hydrocarbon information from organic-rich rock samples. In step 100, drilling core or cutting samples are collected at the well site. The samples may be cleaned on-site (such as by washing with water) in order to minimize contamination from the drilling mud. The samples are then transferred to a container (such as Isojar, a commercially available jar designed specifically for rock samples), and sealed, such as by a lid or similar covering. Each container may contain a single sample or multiple samples; in the latter case, the multiple samples should be samples from the same geologic interval. Rock samples from different geologic intervals should be collected in different containers to protect the unique geochemical fingerprints of each interval.

In step 102, the sealed container or containers with rock samples are transported to the laboratory, ideally but not necessarily in low-temperature conditions to prevent the vaporization of the light-end hydrocarbons. The low-temperature condition is usually achieved by placing the container on dry-ice or similar material.

In step 104, the rock samples are prepared at the laboratory. Initially, the samples may be carefully removed from the container and rapidly washed three times or more using water or saturated water-based solution of potassium chloride to further remove any contamination from the drilling mud. The cleaned samples may be air dried to remove excess water.

Some or all of each sample may be selected for further preparation. For example, a portion of the interior of a particular sample may be used, as interior material in the sample may be less adversely affected (such as by loss of hydrocarbons) during collection and transport of the sample.

Each sample is prepared by a process of grinding, homogenizing, and sieving through meshes of appropriate sizes to achieve the desired mesh size or sizes suitable for different variations of the methods and devices described herein. In an exemplary embodiment, the desired size is approximately 20-25 mesh (i.e., approximately 0.71 mm to approximately 0.84 mm). The process includes and results in homogenizing the sample material. The smaller sample material size exposes a larger surface area of the organic-rich rock that enables and enhances the following extraction process or process. In an exemplary embodiment, the grinding process may comprise cryo-milling, i.e., grinding or milling in a cryo-condition under $N_2$ or in cooler conditions. The cryo-condition during the grinding process helps prevent excessive vaporization of light-end hydrocarbons.

In step 106, hydrocarbons are extracted from the prepared rock sample for subsequent analysis 108. In several exemplary embodiments, a small amount of the prepared sample is placed in an extraction device (such as that described below and illustrated in FIGS. 4-6) to allow extraction of hydrocarbon from the shale rock samples for geochemical fingerprinting analysis. In one exemplary embodiment, the amount of prepared sample used is 0.5 grams or less.

Figure 2:
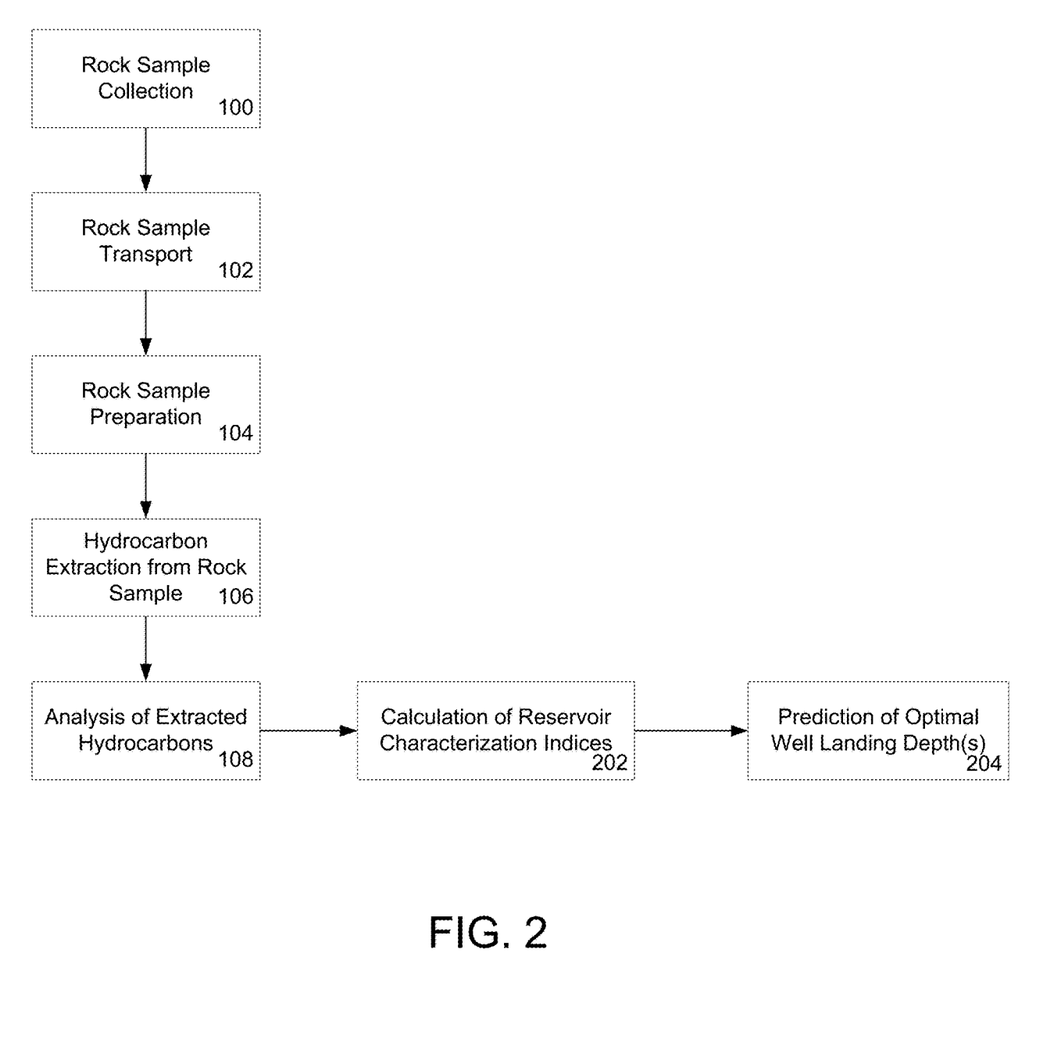
FIG. 2 is a flowchart illustrating the basic steps of additional exemplary embodiments of the present inventive methods, directed towards optimizing well placement in a reservoir based on hydrocarbon and rock properties derived from information collected from hydrocarbons extracted from organic-rich rock.
Figure 3:
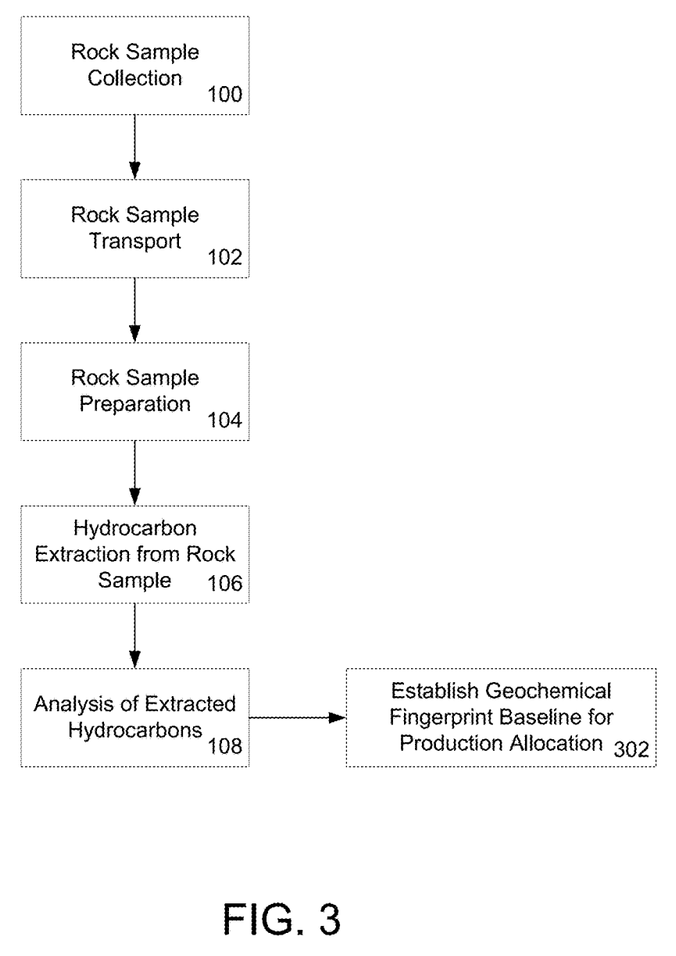
FIG. 3 is a flowchart illustrating the basic steps of additional exemplary embodiments of the present inventive methods, directed towards establishing a geochemical fingerprint baseline, using hydrocarbon information extracted from organic-rich rock, for production allocation in an unconventional reservoir.

In step 108, the extracted hydrocarbon or hydrocarbons are chemically analyzed to collect geochemical fingerprints (as described in further detail below). The geochemical fingerprinting results collected from the rock samples are used for various application, including, but not limited to, unconventional reservoir characterization, unconventional reservoir monitoring, completion optimization, and the like. For example, as seen in FIG. 2, in one embodiment the geochemical fingerprint data are used to conduct data mining and data analytics work (typically using or conducted through a computer program, software, software application, script, code, or similar product) to determine, calculate and provide subsurface reservoir and/or fluid characterization (such as calculation of reservoir characterization indices) 202, and/or prediction of optimal well landing depths 204. In another embodiment, as seen in FIG. 3, the collected hydrocarbon information from the rock samples may be used together with geochemical fingerprints from produced oil or hydrocarbon samples to establish a geochemical fingerprint baseline for production allocation and provide monitoring of fluid flow in the unconventional reservoir 302.

Figure 4:
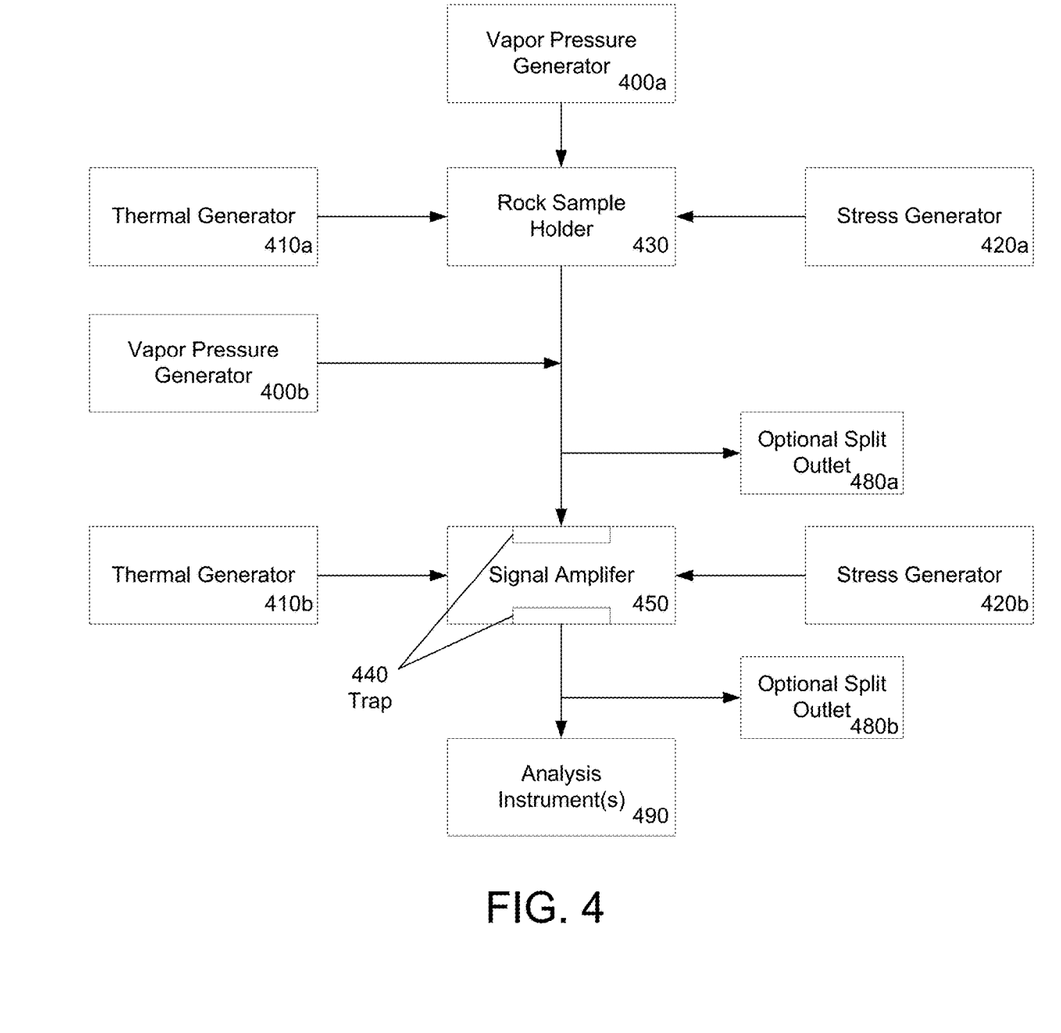
FIG. 4 is a general schematic of an analytical apparatus comprising the main features needed for implementing the present inventive method in accordance with an exemplary embodiment of the present invention.
Figure 5:
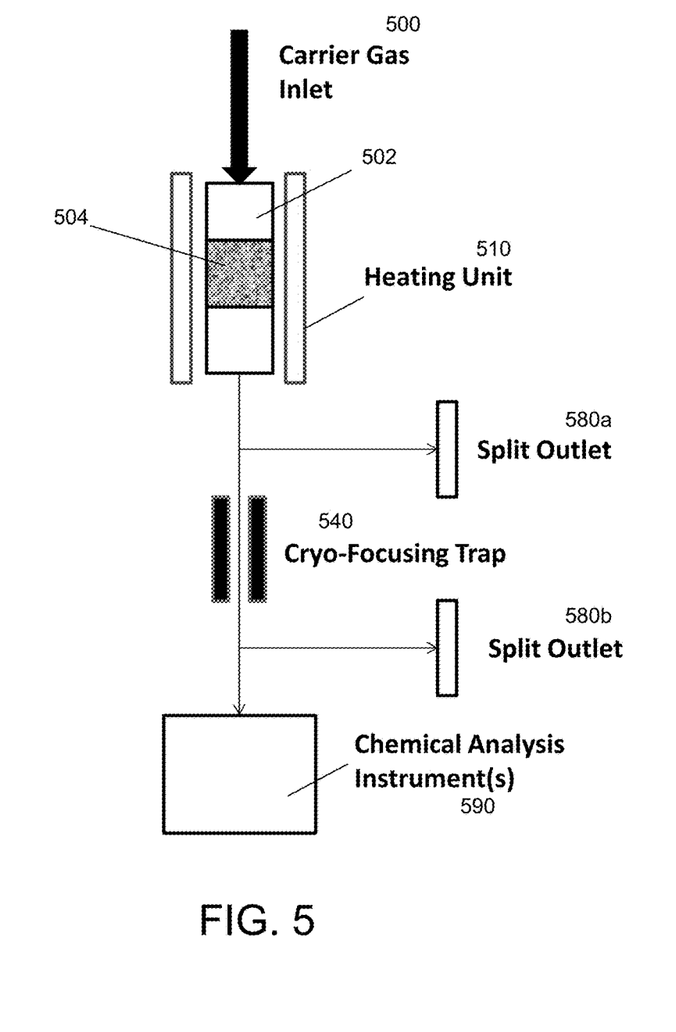
FIG. 5 illustrates an alternative method of using the present invention by using only thermal desorption and carrier gas to extract the hydrocarbons from the sample, in accordance with another exemplary embodiment of the invention.
Figure 6:
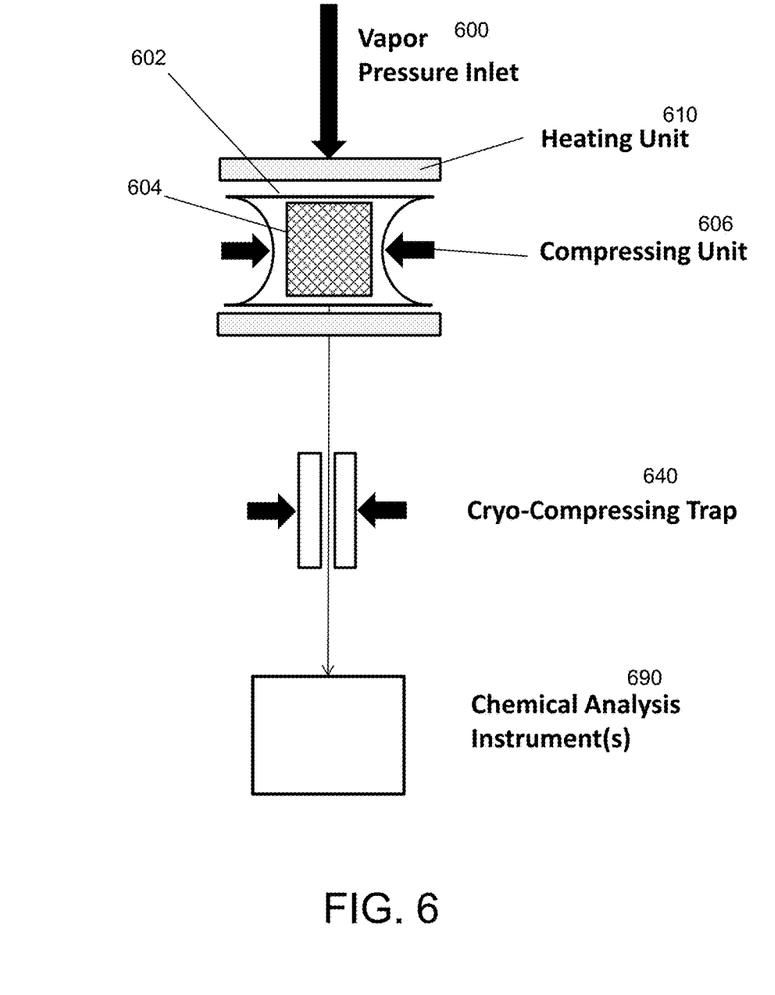
FIG. 6 illustrates an alternative method of using the present invention by using mechanical stress, thermal desorption and vapor pressure to extract the hydrocarbons from the sample, in accordance with another exemplary embodiment of the invention.

FIGS. 4-6 show exemplary embodiments of a hydrocarbon extraction system and device in accordance with the present invention.

In FIG. 4 high-pressure vapor (typically hydrogen or helium gas) pressurized from a vapor pressure generator 400a flows through the rock sample holder 430 where the sample may be simultaneously heated by a thermal generator 410a and compressed mechanically by a stress generator 420a, causing hydrocarbon(s) to be extracted in gas form from the sample. The extracted hydrocarbon is then carried by the vapor (vapor pressure may be maintained after extraction by vapor pressure generator 400b) to pass through a signal amplifier 450 where the hydrocarbon is trapped (separated from the carrier vapor) and amplified to allow injection into one or more chemical analysis devices or instruments 490. The chemical analysis devices or instruments 490 (and 590 and 690 from FIGS. 5-6) may be, but are not limited to, comprehensive two-dimensional gas chromatography with mass spectrometry (GC×GC-MS), comprehensive two-dimensional liquid chromatography (LC×LC), gas chromatography with isotope ratio mass spectrometry (GC-IRMS), fluorescence spectrometry, and electromagnetic scattering spectroscopic measurement such as Ramen spectroscopy.

An optional split outlet or outlets may be designed both before 480a and after 480b the signal amplifier. The split outlets divert and re-collect additional extracted hydrocarbon for other measurements or analysis. An optional cryo-focusing trap 440 is added during signal amplification to further sharpen the signal in the extracted hydrocarbon into the measurement unit 490. Temperature and pressure during signal amplification may be provided or maintained at the desired values by thermal generator/cooler 410b and stress generator 420b. The temperature used in the thermal generator(s) 410a, b and cryo-focusing trap 440 may be adjusted depending on the hydrocarbon range of interest. For example, if gas range hydrocarbons, such as methane and ethane, are of interest, then the temperature used in the cryo-focusing trap may be as low as −190 degrees Celsius.

FIG. 5 illustrates an alternative method of using the present invention by using only thermal desorption and carrier gas to extract the hydrocarbons from the sample. The carrier gas 500 (typically hydrogen or helium gas) flows into the inlet of the sample holder 502 holding the rock sample 504 in a programmed thermal desorption (or heating) unit 510 to extract (desorb) hydrocarbon in gas form from the sample. The carrier gas carries the desorbed hydrocarbon over to cryo-focusing trap 540 where the hydrocarbon is trapped and separated from the carrier gas to allow injection into the geochemical fingerprint analysis instruments or devices 590. Split outlets are designed and located both before 580a and after 580b the cryo-focusing trap to divert and collect additional extracted hydrocarbon for other geochemical fingerprint measurements or other analysis.

FIG. 6 illustrates an alternative method of using the present invention by using mechanical stress, thermal desorption and vapor pressure to extract the hydrocarbons from the sample. The vapor 600 (typically hydrogen or helium gas) flows into the inlet of the sample holder 602 holding the rock sample 604 in a programmed thermal desorption (or heating) unit 610 with mechanical stress applied to the sample from a compressing unit 606 to extract (desorb) hydrocarbon in gas form from the sample. The desorbed hydrocarbon is carried over to cryo-focusing-compressing trap 640 (i.e., a cryo-focusing trap as described above with the addition of compression) where the hydrocarbon is trapped and separated from the vapor to allow injection into the geochemical fingerprint analysis instruments or devices 690.

In several embodiments, samples are desorbed at 200-250° C. for 5-10 min with helium gas flowing through the sample at 50-100 mL/min. Released hydrocarbons from samples are captured by a trap containing adsorbents that retain hydrocarbons from C4-C40 range. After sample desorption, the trap is heated to 320° C. to 350° C. for 3-20 min with helium gas flow at 2-20 mL/min to release the hydrocarbons, which are swept onto the GC column and analyzed. Direct desorption can also be used in which no trap is used and the released hydrocarbons from the sample are directly carried by helium gas onto the GC column.

Figure 7A:
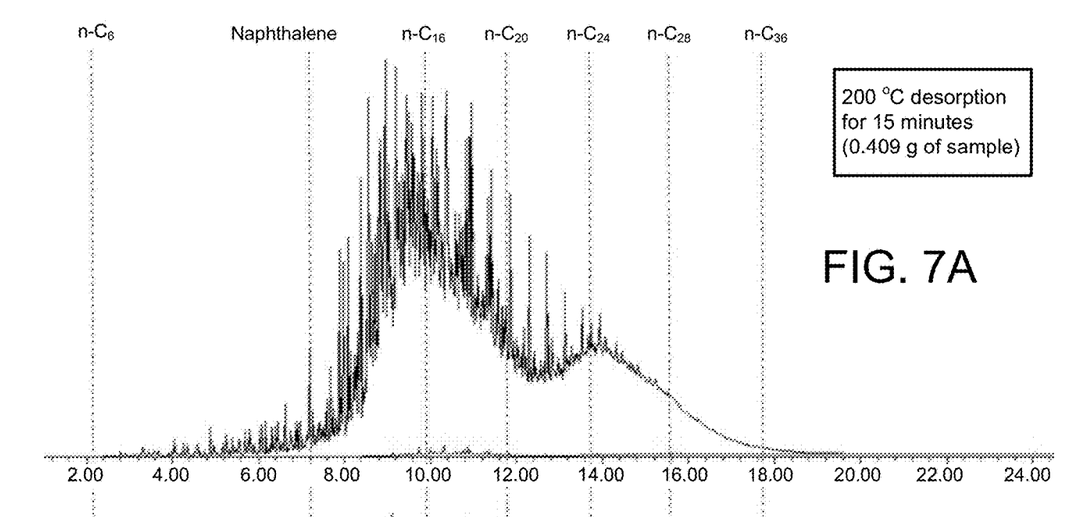
FIGS. 7A and 7B are exemplary graphs showing geochemical information collected using gas chromatography (GC) of hydrocarbon extracted from an organic-rich rock sample using the methods described herein with different programmed temperature settings.
Figure 7B:
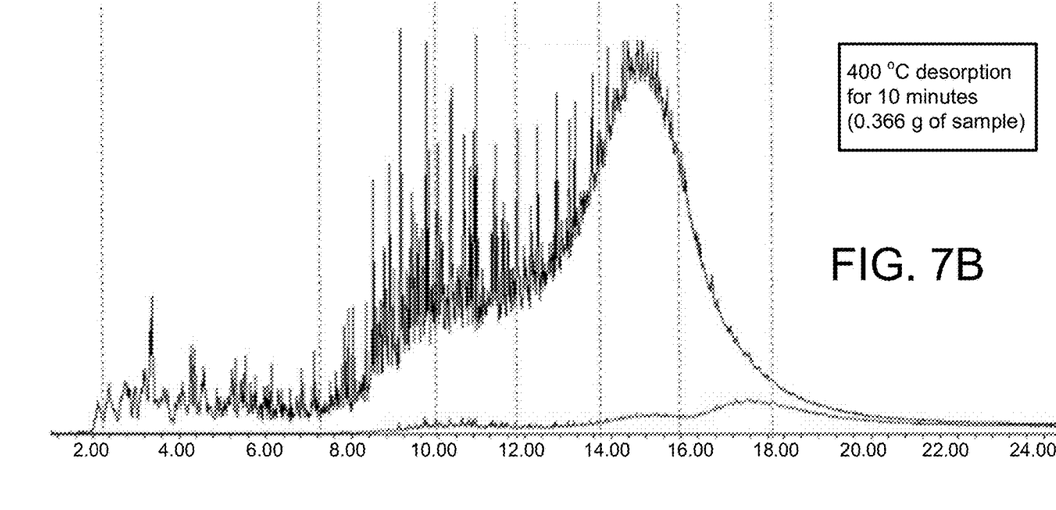

FIGS. 7A and 7B illustrate sample geochemical fingerprinting graphs showing geochemical information collected using gas chromatography (GC) of hydrocarbon extracted from an organic-rich rock sample using the methods described herein with different programmed temperature settings.

Geochemical information collected using 2D gas chromatography (2DGC) of hydrocarbons extracted from an organic-rich core sample using the methods described herein with different programmed temperature settings illustrates the range of information (i.e., lower carbon numbers) that would have been lost by using traditional prior-art Soxhlet extraction techniques. The current invention is able to preserve and provide information down to carbon number 7-8 range, while the Soxhlet method only preserves and provides information down to carbon number 12-15.

Figure 8:
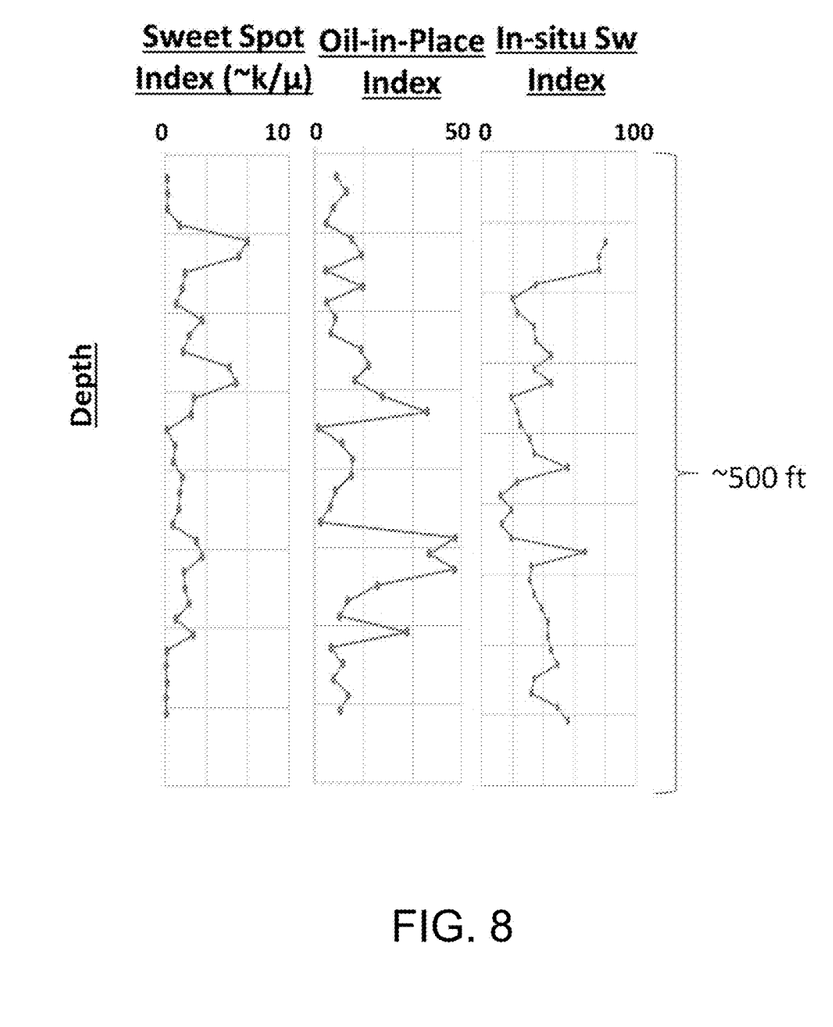
FIG. 8 illustrates the use of the present invention to calculate a group of subsurface reservoir characterization indices to optimize horizontal well placement in an unconventional reservoir.

FIG. 8 illustrates the use of the present invention to calculate a group of subsurface reservoir characterization indices (shown over a depth range of 500 feet) that may be used to optimize horizontal well placement in an unconventional reservoir. Indices shown are sweet spot index, oil-in-place index, and in-situ water saturation (Sw) index. However, such indices also may include, but are not limited to, reservoir quality index, oil-in-place index, in-situ water saturation index, fluid viscosity index, fluid mobility index, and geomechanics index.

Figure 9:
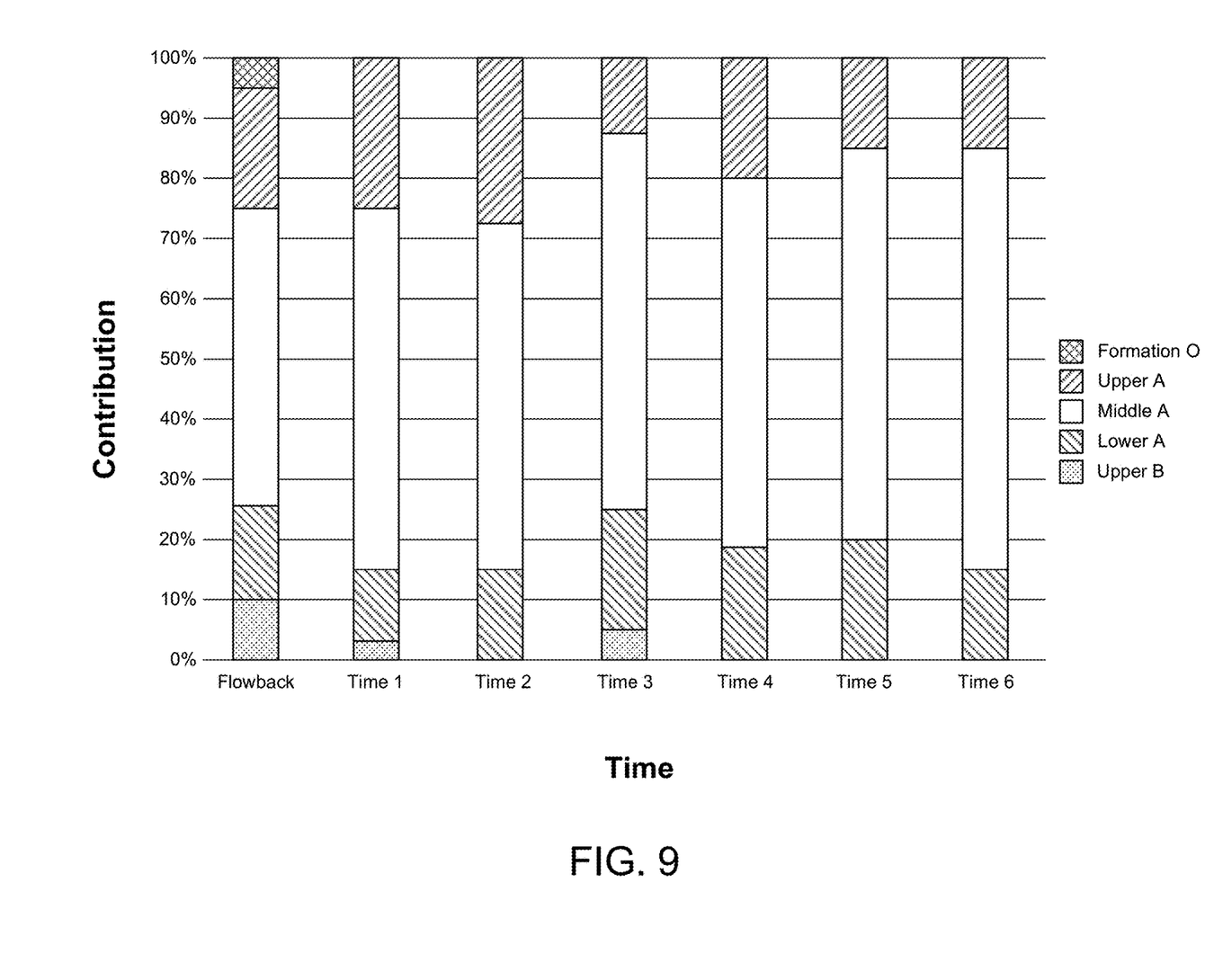
FIG. 9 illustrates the production allocation results in an unconventional reservoir by using the present invention to establish a baseline using hydrocarbon extracted from organic-rich rock cutting samples.

FIG. 9 illustrates an example of a chart showing production allocation results (as a percentage of contribution from subsurface formations for hydrocarbon production at or during a particular time or time interval) in an unconventional reservoir by using the present invention to establish a baseline using hydrocarbon extracted from organic-rich rock cutting samples from the reservoir. Production allocation measures may include, but are not limited to, zone-specific production contribution, drainage frac height evaluation, and well production sharing and communication evaluation.

Figure 10:
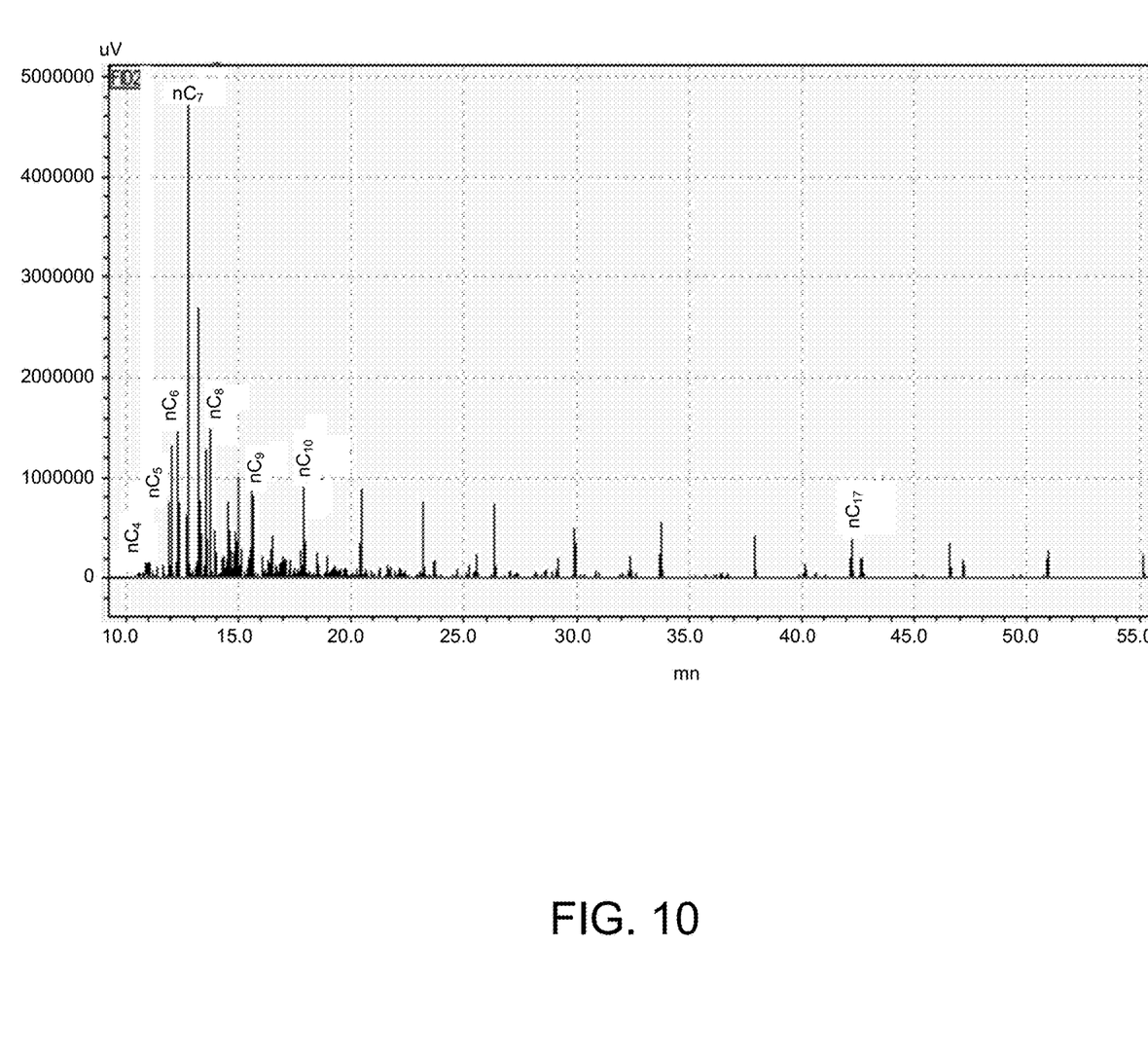
FIG. 10 shows a gas chromatogram of a geochemical fingerprint collected from a preserved shale cutting sample using the method described herein.

FIG. 10 shows a gas chromatogram of a geochemical fingerprint collected from a preserved shale cutting sample using the method described herein, showing information being preserved from as low as carbon number 4-10 range.

The tubular sample holder may be made of glass, with prepared rock sample placed in the center, with quartz wool loosely placed at the two ends to hold the samples in place while allowing carrier gas (as described above) to pass through.

Non-limiting examples of the above-described methods, systems, and devices are provided below:

Example 1—Use of the Method to Collect Geochemical Fingerprint Data from Organic-Rich Drill Cutting Samples to Determine Optimal Horizontal Well Landing Depth The following description provides an example of one set of conditions that may be applied to extract hydrocarbons from typical organic-rich rock core samples to calculate a group of subsurface reservoir characterization indices to assist in a horizontal well landing depth decision.

Approximately 10 grams of the interior piece of an organic-rich shale rock core sample was collected. The sample was ground, homogenized, and sieved to select the desired mesh-sized samples. A small amount (approximately 0.05 to 0.2 grams) of prepared sample was packed in a sample tube (the exact loading amount depends on the organic-richness of the rock). The packed sample tube was loaded in a set of instruments similar to those shown in FIG. 4, consisting of a Markes TD 100-xr with a built-in cold-trap and a GC×GC-FID device of Shimadzu GC2030 equipped with thermal modulator of Zoex II by Zoex Corporation. Desired geochemical fingerprint data was collected from the hydrocarbon extracted from the sample using a 2D-GC device by Shimadzu GC2030 equipped with thermal modulator of Zoex II by Zoex Corporation. As shown in FIG. 6, molecular geochemical analyses by 2D-GC provided geochemical fingerprint information from as low as C7 was extracted effectively using the method herein. This was repeated for 80 samples, collected at depths of interest from approximately 8,000 to 11,000 ft.

The collected geochemical fingerprint information of each sample was then fed into an in-house computer program to calculate the reservoir quality ("sweet spot") index, oil-in-place index, and in-situ water saturation (Sw) index (as seen in FIG. 10). Those indices provided critical subsurface reservoir information such as reservoir quality, water saturation, and oil saturation, which lead to decision on the landing depths for a number of horizontal wells.

Example 2—Use of the Method to Collect Geochemical Fingerprint Data from Organic-Rich Drill Cutting Samples for Production Allocation The following description provides an example of one set of conditions that may be applied to extract hydrocarbons from organic-rich shale drill cutting samples to establish as baselines for an unconventional reservoir production allocation work.

Approximately 30 grams of each cutting sample was collected for a plurality of end member production zones. The cutting samples were lighted rinsed, and sealed on the drilling site, and transported to the laboratory in glass containers. The samples were cleaned, ground, homogenized, and sieved to select the desired mesh-sized samples. A small amount (approximately 0.05 to 0.2 grams) of prepared sample was packed in a sample tube (the exact loading amount depends on the organic-richness of the rock). The packed sample tube was loaded in a set of instruments similar to those shown in FIG. 3, consisting of a Shimadzu TD 30 with a built-in cold-trap and a GC×GC-FID device of Shimadzu GC2030 equipped with thermal modulator of Zoex II by Zoex Corporation. Desired geochemical fingerprint data was collected from the hydrocarbon extracted from the sample using the GC×GC-FID device of Shimadzu GC2030 equipped with thermal modulator of Zoex II by Zoex Corporation.

Produced oil samples also were collected from the producing wells in the same reservoir in time sequence. The produced oil samples also were analyzed to produced geochemical fingerprint information. The collected geochemical fingerprint information of each cutting and produced oil sample was fit into a computer program to calculate production contribution from each of the end member zones. The production allocation results are illustrated in FIG. 9, and demonstrate the end member zones from which the produced oil was produced, and the percentage of their contribution. This information was subsequently used to make critical field development decisions, such as how to space and stack multiple wells in the same reservoir for maximum return. In this specific example, drilling two layers of horizontal wells were not effectively draining all the hydrocarbons in the approximately 500 foot stacked play. Therefore, based on the finding, a third layer of well was proposed to be drilled.

Example 3—Use of the Method to Preserve and Collect Light Hydrocarbon Geochemical Fingerprint from a Shale Cutting Sample The following description provides an example of one set of conditions that may be applied to preserve and extract light hydrocarbons from typical organic-rich shale cutting samples to collect geochemical fingerprints.

Approximately one-half cup of an organic-rich shale rock cutting sample was collected on the drill site. The cutting sample was rapidly rinsed with tap water three times to remove the drilling mud. The cleaned cutting sample was transferred to a glass Isojar container, sealed, and placed on dry ice to transport to the lab as fast as possible. After arriving at the lab, the cutting sample was immediately cryo-milled under $N_2$ gas (at approximately −40° C.) to minimize any light hydrocarbon loss, then homogenized, and sieved to select the desired mesh-sized (40-80 mesh) samples. A small amount (approximately 0.05 to 0.2 grams) of prepared sample was packed in a sample tube (the exact loading amount depends on the organic-richness of the rock). The packed sample tube was loaded in a set of instruments similar to those shown in FIG. 4, consisting of a Markes TD 100-xr with a built-in cold-trap and a GC×GC-FID device of Shimadzu GC2030 equipped with thermal modulator of Zoex II by Zoex Corporation. Desired geochemical fingerprint data was collected from the hydrocarbon extracted from the sample using the above devices.

As seen in FIG. 9, molecular geochemical analyses by GC demonstrates that geochemical fingerprint information from as low as $C_4$ was preserved and extracted effectively from a cutting sample using the method herein. The gas composition of methane, ethane, and propane from this cutting sample was also preserved and was able to be measured using the method described herein by adding an ultra-low temperature liquid $N_2$ cold trap (at approximately −90° C.) to trap the gas released from the cutting sample.

Further details of the above examples are illustrated in U.S. Provisional Application No. 62/661,109, filed Apr. 23, 2018, which is incorporated herein by specific reference in its entirety for all purposes.

It should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:

1. A method for collecting hydrocarbon information from organic-rich rock samples, comprising the steps of:
   obtaining a rock sample;
   prior to extracting hydrocarbons in gas form using a thermal desorption process, processing the rock sample;
   preserving hydrocarbons in the rock sample during the step of processing by processing the rock sample under low temperature conditions at approximately −40° C.;
   extracting hydrocarbons in gas form from the processed rock sample using the thermal desorption process in conjunction with a carrier gas or vapor;
   trapping the extracted hydrocarbons from the carrier gas or vapor; and
   analyzing the trapped, extracted hydrocarbons.

2. The method of claim 1, wherein the rock sample comprises a drill core or drill cutting.

3. The method of claim 1, wherein the rock sample comprises a shale rock sample.

4. The method of claim 1, further comprising the steps of:
   obtaining the rock sample from a drill site;
   sealing the sample in a container at the drill site; and
   transporting the sealed container in low-temperature conditions on dry ice to a laboratory.

5. The method of claim 1, wherein the step of extracting hydrocarbons further comprises using vapor pressure and mechanical stress applied to the processed rock sample.

6. The method of claim 1, where the step of processing the rock sample under low temperature conditions comprises the step of cryo-milling the rock sample or portions thereof under $N_2$.

7. The method of claim 1, wherein the thermal desorption process comprises using a programmed heating unit to heat the processed rock sample, and a cryo-focusing trap with variable temperature.

8. The method of claim 7, wherein the variable temperature of the cryo-focusing trap is set based on a hydrocarbon range of interest.

9. The method of claim 8, wherein the temperature of the cryo-focusing trap is set at −190 degrees C.

10. The method of claim 1, wherein the step of analyzing comprises the step of obtaining hydrocarbon information for the extracted hydrocarbons.

11. The method of claim 10, wherein the hydrocarbon information comprises hydrocarbon geochemical fingerprinting.

12. The method of claim 10, further comprising one or more of the following steps:
   calculating a group of reservoir characterization indices based on the extracted hydrocarbon information;
   predicting an optimal horizontal well landing depth based on the extracted hydrocarbon information; and/or
   establishing a geochemical fingerprint based for a sampled depth based on the extracted hydrocarbon information.

13. The method of claim 10, wherein said hydrocarbon information comprises one or more of: organic compound absolute concentration; organic compound absolute mass; organic compound relative concentration; organic compound relative mass; and/or derived fluid properties.

14. The method of claim 10, wherein said hydrocarbon information comprises one or more of: elemental absolute concentration; elemental relative concentration; elemental absolute mass; elemental relative mass; and/or elemental isotopic ratios.

15. The method of claim 10, wherein the step of analyzing further comprises using one or more of the following analysis techniques: comprehensive two-dimensional gas chromatography with mass spectrometry (GC×GC-MS); comprehensive two-dimensional liquid chromatography (LC×LC); gas chromatography with isotope ratio mass spectrometry (GC-IRMS); fluorescence spectrometry; and/or electromagnetic scattering spectroscopic measurement.

* * * * *